United States Patent [19]

Metcalf et al.

[11] Patent Number: 4,524,076

[45] Date of Patent: Jun. 18, 1985

[54] NOVEL γ-AMINOBUTYRIC ACID TRANSAMINASE INHIBITORS

[75] Inventors: Brian W. Metcalf, Mason; Bruce J. Lippert, Cincinnati, both of Ohio

[73] Assignee: Merrell Dow Pharmaceuticals Inc., Cincinnati, Ohio

[21] Appl. No.: 663,250

[22] Filed: Oct. 22, 1984

Related U.S. Application Data

[63] Continuation of Ser. No. 597,799, Apr. 6, 1984, abandoned, which is a continuation of Ser. No. 540,743, Oct. 11, 1983, abandoned.

[51] Int. Cl.$^3$ .................... A61K 31/34; C07D 307/89
[52] U.S. Cl. .................................... 514/472; 549/480
[58] Field of Search ..................... 549/480; 424/285

[56] References Cited

U.S. PATENT DOCUMENTS

| | | | |
|---|---|---|---|
| 3,306,899 | 2/1967 | Dowbenko | 549/480 |
| 3,347,872 | 10/1967 | Passannante et al. | 549/480 |
| 3,983,134 | 9/1976 | Matsui et al. | 549/480 |

*Primary Examiner*—Alan Siegel
*Attorney, Agent, or Firm*—Raymond A. McDonald; Stephen L. Nesbitt; Gary D. Street

[57] ABSTRACT

This application relates to 4-amino-4,5-dihydro-2-furancarboxylic acid, and esters thereof, useful as γ-aminobutyric acid transaminase inhibitors.

11 Claims, No Drawings

NOVEL γ-AMINOBUTYRIC ACID TRANSAMINASE INHIBITORS

This is a continuation of application Ser. No. 597,799, now abandoned filed Apr. 6, 1984 which is a continuation of application Ser. No. 540,743 filed Oct. 11, 1983 now abandoned.

This invention relates to 4-amino-4,5-dihydro-2-furancarboxylic acid, its lower alkyl esters, the pharmaceutically acceptable salts thereof, to their use as chemotherapeutic agents, and to the chemical processes and intermediates useful in the preparation thereof.

More specifically, this invention relates to γ-aminobutyric acid transaminase inhibitors useful in the treatment of epilepsy. These inhibitors are of the formula

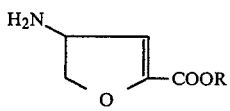

including the individual enantiomers and racemic mixtures thereof, and the pharmaceutically acceptable salts thereof, wherein R is hydrogen or a $C_{1-6}$ lower alkyl radical.

The preparation of the compounds of this invention may be achieved by the judicial selection of the appropriate starting materials followed by the application of chemical reactions and techniques analogously known in the art.

One such process for preparing the (R), (S) or (RS) racemic mixtures thereof is by employing the selected optical isomer, or racemic mixture thereof, of arabinose as a starting material. In each instance the chemical reaction of the sequential series of steps of chemical reactions would be the same but for the stereoisomers, or mixtures produced. For example, starting with L-arabinose that optical isomeric form would be maintained throughout the process to finally produce the (S) enantiomer of the desired product. Similarly, starting with D-arabinose will ultimately produce the (R) enantiomer. Thus, although throughout the description and specific exemplification of the process for preparing the 4-amino-4,5-dihydro-2-furancarboxylic acid and esters of formula I from arabinose the L isomer is utilized, it is to be understood that such description and exemplication embraces the obtention of both the optical isomers and the mixtures thereof.

In the process starting with L-arabinose it is convenient to convert arabinose to a triol according to the method described for the D-isomer by Rabinson and Fletcher, (J.O.C. 32, 3452, 1968). The so-obtained triol is selectively silylated to protect the 2-position primary alcohol by standard reaction conditions utilizing t-butyl dimethylsilyl chloride in the presence of trimethylene and dimethylaminopyridine, the reaction being effected at room temperature. Following this selective silylation both the 3- and 4-position hydroxy groups are protected with mesylate leavening groups by standard reaction with mesylchloride to form a bismesylate.

Following the bis-mesylation, reaction of the 2-[[(1,1-dimethylethyl)dimethylsilyl]oxy]tetrahydro-3,4-furandiol-bis-(methylsulfonate) with sodium azide will selectively displace the 4-position mesylate to form the desired azide. Following that step the 2-position primary alcohol is liberated by removal of the silyl protecting group and the resulting alcohol is subjected to esterification, preferably forming a methyl ester, although other esters may optionally be formed. Elimination of the remaining 3-position mesyl group by reaction with triethylamine at room temperature will form the desired 2,3-double bond and the resulting methyl-4-azido-4,5-dihydro-2-furancarboxylate is chemically reduced to the amine by reaction with triethylamine and propanethiol. Alternatively, the reduction of the azide may be effected with a hydrogen Lindlar catalyst using ethanol as a solvent. Following the reduction of the azide the ester is hydrolyzed by reaction with lithium hydroxide and methanol at room temperature.

A process which yields only the racemic mixture of the desired compounds of this invention (Formula I) advantageously utilizes 2-furoic acid as the starting material.

In the initial step the 2-furoic acid is subjected to chemical reduction to yield 2,5-dihydro-2-furoic acid by reaction with lithium and ammonia in absolute ethanol according to standard reductive conditions. The so-obtained furoic acid is esterified and the resulting ester (preferably the methyl ester), when subjected to silver isocyanate and iodine will yield, in situ, the desired methyltetrahydro-3-iodo-4-isocyanato-2-furancarboxylate. The isocyanate function is converted to a carbamate derivative, (preferably utilizing a p-methoxybenzyl alcohol reactant) to protect the amine function. This reaction is followed by elimination of HI by stirring the iodo compound with diazobicyclooctane in acetone, to form the corresponding 4,5-dihydro compound. Following the formulation of the desired double bond the ester is saponified and the resulting compound is subjected to acid hydrolysis with trifluoroacetic acid in anisole under an inert atmosphere (argon) to convert the carbamate to the free amine.

The foregoing generally described processes are further illustrated by the following examples.

EXAMPLE I (4S)4-Amino-4,5-dihydro-2-furancaroylic acid

Step A:

2-[[(1,1-dimethylethyl)dimethylsilyl]oxy]methyl tetrahydro-3,4-furandiol

Tetrahydro-2-(hydroxymethyl)-3,4-furandiol (10.2 g, 76 mMole), (prepared from L-arabinose as described for the D-isomer by Rabinsohn and Fletcher, J.O.C., 32, 3452, 1968) in THF (100 ml) containing triethylamine (8 g, 80 mMole, 11.4 ml) and dimethylaminopyridine (100 mg) is treated dropwise with t-butyl dimethylsilyl chloride (12.0 g, 80 mMole) in THF (20 ml). The mixture is stirred at room temperature for 16 hours, then diluted with ether, filtered and concentrated. The product (12.2 g) is isolated by flash chromatography on silica gel using ethyl acetate-hexane (3:1) as eluant.

Step B:

2-[[[(1,1-dimethylethyl)dimethylsilyl]oxy]methyl]tetrahydro-3,4-furandiol bis(methylsulfonate)

To the diol (12.2 g, 49.1 mMole) in $CH_2Cl_2$ (200 ml) containing triethylamine (12.0 g, 120 mMole, 17 ml) at 0° is added mesyl chloride (12.5 g, 8.5 ml) and the mixture stirred at room temperature overnight. The mixture is then washed with water, $NaCO_3$ solution, dried and concentrated. The bismesylate (16.0 g) is isolated by flash chromatography on silica gel using 30% ethyl acetate hexane as eluant.

Step C: 4-Azido-2-[[[(1,1-dimethylethyl)dimethylsilyl]oxy]methyl]tetrahydro-3-furanol methylsulfonate To the bismesylate (16.0 g, 49 mMole) in DMF (70 ml) is added NaN₃ (6.2 g, 55 mMole) and the mixture heated at 93° for 20 hours. The mixture, on cooling, is poured into water and extraced with ether. The azide (5.6 g) is isolated by flash chromatography using 25% ethyl acetate as eluant.

Step D: Methyl 4-azidotetrahydro-3-[(methylsulfonyl)oxy]-2-furancarboxylate

The silyl ether (5.6 g, 16 mMole) in THF (50 ml) is treated with (nBu)₄NF (18 ml of a 1M solution) for 2 hours at room temperature. The solution is then diluted with CH₂Cl₂ and washed with brine. Flash chromatography on silica gel using ethyl acetate as eluant afforded the alcohol (3.3 g). This is dissolved in acetone (15 ml) and treated with an excess of Jones reagent for 16 hours. The acetone is evaporated off at room temperature, the residue treated with brine (15 ml) and extracted well with CH₂Cl₂. The organic phase is dried and concentrated, then treated with an ethereal solution of diazomethane. Flash chromatography using ethyl acetate as eluant afforded the ester (1.6 g).

Step E: Methyl 4-azido-4,5-dihydro-2-furancarboxylate

To the ester (1.6 g) in CH₂Cl₂ (20 ml) is added trietyl amine (2 ml) and the solution is stirred for 24 hours at room temperature, then concentrated. The product (600 mg) is isolated by flash chromatography using 20% ethyl acetate hexane as eluant.

Step F: 4-Amino-4,5-dihydro-2-furancaroylic acid

The azide (500 mg, 2.96 mMole) in methanol (10 ml) is treated with triethylamine (400 mg) and propanedithiol (432 mg, 4 mMole) for 48 hours. The mixture is then filtered and concentrated. The residue is treated with methanol (5 ml) and 1N LiOH (5 ml) for 24 hours at room temperature. It is then diluted with water (15 ml) and extracted with CH₂Cl₂. The aqueous phase is acidified and extracted with CH₂Cl₂. The aqueous phase is then concentrated under reduced pressure. The residue is diluted with water, neutralized by the addition of 1N NH₄OH and applied to a Dowex AG 50W-X8 resin in the acid form. The column is eluted with water, then with 1N NH₄OH. Concentration of the NH₄OH eluate affords the amino acid (110 mg) which is recrystallized from acetone/water to give 86 mg.

EXAMPLE II

4-Amino-4,5-dihydro-2-furancarboxylic acid

Step A: 2,5-Dihydro-2-furancarboxylic acid

Into a three-neck one liter flask, fitted with a dry ice-acetone condenser and cooled in a dry ice-acetone bath, was condensed 750 ml of ammonia. 2.5 g of sodium metal was then added and the resultant blue-black solution stirred for 15 minutes before distilling off 500 ml of ammonia into a similarly fitted second flask. 2-Furoic acid (15 g, 0.133 mole), dissolved in 90 ml of absolute ethanol, was then added by syringe to the stirred, distilled ammonia and the cooling bath removed. Lithium wire (2.8 g, 0.40 mole) was added in small pieces. The resultant blue color quickly faded as the ammonia reached reflux. The ammonia was then removed by distillation and the reaction residue placed under high vacuum for several minutes. After the last traces of ammonia had been removed, 100 ml of water was added to the residue and the pH adjusted to 8 using 6M HCl. Methylene chloride (300 ml) was then added followed by enough 6M HCl to bring the pH of the aqueous phase to 2. The organic phase was separated and the aqueous phase extracted once more with methylene chloride. Ether was then added, the aqueous phase saturated using solid sodium chloride and the layers separated. The combined organic extracts were then dried over magnesium sulfate, filtered and concentrated at ambient temperature to afford an oil (10.6 g).

Step B: Methyl-2,5-dihydro-2-furancarboxylate

Dicyclohexylcarbodiimide (19.2 g, 92.9 mole) was suspended in 250 ml of methylene chloride and 4.2 ml of methanol syringed in. The stirred mixture was then chilled in an ice bath and the acid (10.6 g, 92.9 mMole) added as a solution in 50 ml of methylene chloride. Dimethylaminopyridine (1.1 g, 9.3 mMole) was added and the cooling bath removed. After stirring at room temperature overnight, the reaction mixture was filtered. The filtrate was washed with water, 0.25M HCl and then brine. The organic layer was dried over magnesium sulfate, filtered and concentrated to a small residue which was distilled at 30 mm Hg. The fraction boiling at 90°–104° C. was collected to yield a water white liquid (3.5 g).

Step C: Methyl-tetrahydro-3-iodo-4-isocyanate-2-furancarboxylic

The ester (3.8 g, 30 mMole) was dissolved in 50 ml of methylene chloride and chilled in an ice bath. Freshly prepared silver isocyanate (4.9 g, 33 mMole) was added to the stirred solution followed by iodine (7.6 g, 30 mMole). The reaction was stirred at 0° C. for 1 hour and then at room temperature for 3 hours. The reaction mixture was then filtered through celite, the celite pad washed with ether and the filtrate concentrated to a purple, oily solid (10 g) which was used without further purification in the next step.

Step D: Methyl-tetrahydro-3-iodo-4-[[[(4-methoxyphenyl)methoxy]carbonyl]amino]-2-furancarboxylate To the crude iodide (10 g) was added 3.8 ml of p-methoxybenzyl alcohol and the mixture stirred at room temperature overnight. Chromatography, using 25% ethyl acetate-hexane, gave the desired product as a mixture of isomers (5.96 g).

Step E: Methyl-4,5-dihydro-3-iodo-4-[[[(4-methoxyphenyl)methoxy]carbonyl]amino]-2-furancarboxylate To the iodo compound (5.96 g), in 50 ml of acetone, was added 1.7 g of diazobicyclooctane. The mixture was stirred at room temperature in the dark, overnight and then filtered. The filtrate was diluted with ether and water, the layers separated and the organic phase washed with water, 0.1M HCl and then brine. The organic layer was dried over magnesium sulfate, filtered and concentrated to give a white oily solid. Chromatography, using 35% ethyl acetate-hexane, afforded the desired compound as a white solid (1.97 g).

Step F:
4,5-Dihydro-4-[[[(4-methoxyphenyl)methoxy]carbonyl]amino]-2-furancarboxylic acid The carbamate (500 mg, 1.6 mMole) was dissolved in 5 ml of tetrahydrofuran and 8 ml of methanol and chilled in an ice bath. Lithium hydroxide (3.6 ml of a 1M aqueous solution) was then added dropwise to the stirred solution. The reaction mixture was stirred at 0° C. for two hours after the addition and then poured into 100 ml of ethyl acetate and 50 ml of a mixture composed of (8:1:1) brine:water:1M HCl. The layers were separated and the organic phase was washed once with brine before being dried over magnesium sulfate, filtered and concentrated to give a white solid (447 mg).

Step G: 4-amino-4,5-dihydro-2-furancarboxylic acid

The acid (447 mg) was suspended in 6 ml of anisole under argon and chilled in an ice bath. To the stirred suspension was added trifluoroacetic acid (10 ml) dropwise. After the addition was completed, the cooling bath was removed and the reaction mixture stirred at room temperature for 1 hour. The reaction mixture was concentrated at ambient temperature and the residue placed under high vacuum to give an oil material. Hexane was added to the oil residue, stirred for several minutes and then decanted. This process was repeated once more. 150 ml of ether was then added and the mixture stirred at room temperature overnight. The supernatant liquid was decanted from the white solid which resulted, additional ether added and the mixture filtered. A white solid, weighing 187 mg after drying in a vacuum desiccator, was obtained.

Illustrative of the pharmaceutically acceptable salts of the compounds of this invention include nontoxic acid addition salts formed with inorganic acids, such as, hydrochloric, hydrobromic, sulfuric and phosphoric acid, and organic acids such as methane sulfonic, salicylic, maleic, malonic, tartaric, citric, and ascorbic acids; and non-toxic salts formed with inorganic or organic bases such as those of alkali metals, for example, sodium, potassium and lithium, alkaline earth metals, for example, calcium and magnesium, light metals of Group III A for example, aluminum; organic amines such as primary, secondary or tertiary amines, for example, cyclohexylamine, ethylamine, pyridine, methylaminoethanol, ethanolamine and piperazine. The salts can be prepared by conventional means.

As stated above, the compounds of this invention possess the inherent characteristics of inhibiting γ-aminobutyric acid transaminase which results in an increase in brain levels of γ-aminobutyric acid. Thus, the compounds are useful in the treatment of disorders of the central nervous system, particularly that dealing with the function of involuntary movement generally associated with seisure disorders of epilepsy.

The ability of the compounds of this invention to inhibit γ-aminobutyric acid transaminase and raise brain GABA levels is determined in vitro by the methods of Lippert et al. (Eur. J. Biochem. 71:441, 1977) and in vivo by Jung et al. (J. Neurochem. 28:717, 1977). γ-Aminobutyric acid levels are markedly increased in mouse brains after treatment with compounds of this invention at doses ranging from 0.5 mg/kg to 10 mg/kg of body weight by parenteral or oral routes. This ability is further demonstrated by the protective effect (anti-epileptic), at doses ranging from 0.5 mg/kg to 25 mg/kg, against convulsions elicited by an intravenous dose of 3-mercaptopropionic acid (100 mg) according to the general method described by Sarhan and Seilar, J. Neuroscience Res., 4 (1979) 399–421 which is used to evidence anti-epileptic activity. Therefore, based on the foregoing results, as well as by comparison with other known compounds useful in the treatment of epilepsy the dose range of the compounds of this invention for the treatment of epilepsy is 0.1 mg −25 mg per kilogram of body weight per day, depending upon the age of the patient, severity of the disease state and other factors as determined by the attending diagnostician.

In addition to their use in the treatment of epilepsy, in their effect on the central nervous system the compounds of the invention may also be used in the treatment of schizophrenia, tardive dyskinesia, muscle spasms and, the compounds also exhibit analgesic effects. Standard laboratory methodology, in conjunction with compounds with known chemotherapeutic agents useful for the foregoing, may readily be utilized to determine the optimal doses for each of these indications.

The compounds of this invention can be administered orally or parenterally to animals, particularly warm blooded animals and mammals and humans either alone or in the form of pharmaceutical preparations containing as the active ingredient compounds of this invention to achieve the desired effect. Pharmaceutical preparations containing compounds of this invention and conventional pharmaceutical carriers can be employed in unit dosage forms such as solids, for example, tablets, pills and capsules or liquid solutions, suspensions or elixirs for oral administration or liquid solutions, suspensions and emulsions for parenteral use. The quantity of compounds administered can vary over a wide range to provide from about 0.1 mg/kg to about 300 mg/kg of body weight of the patient per day. Unit doses of these compounds can contain, for example, from about 50 mg to 2000 mg of the compounds and may be administered, for example, from 1 to 4 times daily. Following are illustrative examples of pharmaceutical preparations containing the compounds of this invention:

|   |   | Per Tablet |
|---|---|---|
| (a) | 4-amino-4,5-dihydro-2-furancarboxylic acid | 100.0 mg |
| (b) | wheat starch | 15.0 mg |
| (c) | lactose | 33.5 mg |
| (d) | magnesium stearate | 1.5 mg |

A portion of the wheat starch is used to make a granulated starch paste which together with the remainder of the wheat starch and the lactose is granulated, screened and mixed with the active ingredient (a) and the magnesium stearate. The mixture is compressed into tablets weighing 150 mg each.

An illustrative composition for a parenteral injection is the following wherein the quantities are on a weight to volume basis:

|   |   | Amount |
|---|---|---|
| (a) | 4-amino-4,5-diyhydro-2-furancarboxylic acid | 100.0 mg |
| (b) | sodium chloride | q.s |
| (c) | water for injection to make | 20 ml |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

An illustrative composition for hard gelatin capsules is as follows:

| | Amount |
|---|---|
| (a) 4-amino-4,5-dihydro-2-furancarboxylic acid | 200.0 mg |
| (b) talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

We claim:

1. A compound of the formula

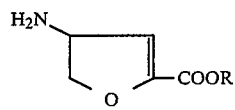

including the individual enantiomers and racemic mixtures thereof, the pharmaceutically acceptable salts thereof, wherein R is hydrogen or $C_{1-6}$ lower alkyl.

2. A compound of claim 1 wherein R is hydrogen.

3. A compound of claim 1 wherein R is $C_{1-6}$ lower alkyl.

4. A compound of claim 3 wherein R is methyl.

5. The (S) enantiomer of a compound of claim 1.

6. The (R) enantiomer of a compound of claim 1.

7. The (S) enantiomer of the compound of claim 2, said compound being (S)4-amino-4,5-dihydro-2-furancarboxylic acid.

8. A method for inhibiting γ-aminobutyric acid transaminase in a patient in need thereof which comprises administering an effective amount of a compound of claim 1.

9. A method for the treatment of epilepsy in a patient suffering from epilepsy which comprises administering an anti-epileptically effective amount of a compound of claim 1.

10. A method for the treatment of schizophrenia in a patient suffering from schizophrenia which comprises administering an effective amount of a compound of claim 1.

11. A method for the treatment of tardive dyskinesia in a patient suffering thereof which comprises administering an effective amount of a compound of claim 1.

* * * * *